US007659990B2

(12) United States Patent
Knighton et al.

(10) Patent No.: US 7,659,990 B2
(45) Date of Patent: *Feb. 9, 2010

(54) ENHANCED OPTICAL COHERENCE TOMOGRAPHY FOR ANATOMICAL MAPPING

(75) Inventors: Robert W. Knighton, Miami, FL (US); Shuliang Jiao, Miami, FL (US); Giovanni Gregori, Coral Gables, FL (US); Carmen A. Puliafito, Pinecrest, FL (US)

(73) Assignee: University of Miami, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/322,607

(22) Filed: Feb. 4, 2009

(65) Prior Publication Data
US 2009/0180123 A1 Jul. 16, 2009

Related U.S. Application Data

(63) Continuation of application No. 11/975,239, filed on Oct. 18, 2007, now Pat. No. 7,505,142, which is a continuation of application No. 11/219,992, filed on Sep. 6, 2005, now Pat. No. 7,301,644.

(60) Provisional application No. 60/632,387, filed on Dec. 2, 2004.

(51) Int. Cl.
*G01B 9/02* (2006.01)
(52) U.S. Cl. .................................... 356/479
(58) Field of Classification Search ............. 356/451, 356/456, 477, 479, 497; 250/227.19, 227.27
See application file for complete search history.

(56) References Cited

U.S. PATENT DOCUMENTS 5,321,501 A 6/1994 Swanson et al. ............ 356/479
5,459,570 A 10/1995 Swanson et al. ............ 356/479
(Continued)

FOREIGN PATENT DOCUMENTS

| CA | 2 390 072 | 12/2003 |
|---|---|---|
| WO | WO 2004/043245 A1 | 5/2004 |
| WO | WO 2004/102112 A1 | 11/2004 |

OTHER PUBLICATIONS

B.A. Bower et al., Rapid Volumetric Imaging of the Human Retina in vivo Using a Low-Cost, Spectral-Domain Optical Coherence Tomography System, *ARVO Annual Meeting May 2, 2005, 8:45 A.M.-9 A. M.*, Program#/Poster#: 1050, printed from website, http://www.abstractsonline.com/viewer/ViewAbstractPrintFriendly on Jul. 26, 2005, 2 pages in length.

(Continued)

*Primary Examiner*—Michael A Lyons
(74) *Attorney, Agent, or Firm*—Morrison & Foerster LLP

(57) ABSTRACT

A system, method and apparatus for anatomical mapping utilizing optical coherence tomography. In the present invention, 3-dimensional fundus intensity imagery can be acquired from a scanning of light back-reflected from an eye. The scanning can include spectral domain scanning, as an example. A fundus intensity image can be acquired in real-time. The 3-dimensional data set can be reduced to generate an anatomical mapping, such as an edema mapping and a thickness mapping. Optionally, a partial fundus intensity image can be produced from the scanning of the eye to generate an en face view of the retinal structure of the eye without first requiring a full segmentation of the 3-D data set. Advantageously, the system, method and apparatus of the present invention can provide quantitative three-dimensional information about the spatial location and extent of macular edema and other pathologies. This three-dimensional information can be used to determine the need for treatment, monitor the effectiveness of treatment and identify the return of fluid that may signal the need for re-treatment.

20 Claims, 2 Drawing Sheets

U.S. PATENT DOCUMENTS

| | | | | |
|---|---|---|---|---|
| 5,465,147 | A | 11/1995 | Swanson | 356/497 |
| 5,921,926 | A * | 7/1999 | Rolland et al. | 600/407 |
| 5,975,697 | A | 11/1999 | Podoleanu et al. | 351/206 |
| 6,201,989 | B1 | 3/2001 | Whitehead et al. | 600/476 |
| 6,769,769 | B2 | 8/2004 | Podoleanu et al. | 351/221 |
| 6,927,860 | B2 | 8/2005 | Podoleanu et al. | 356/479 |
| 7,301,644 | B2 * | 11/2007 | Knighton et al. | 356/479 |
| 7,505,142 | B2 * | 3/2009 | Knighton et al. | 356/479 |
| 2004/0233457 | A1 | 11/2004 | Podoleanu et al. | 356/479 |
| 2004/0239938 | A1 | 12/2004 | Izatt | 365/450 |
| 2006/0072424 | A1 | 4/2006 | Everett et al. | 369/112.01 |
| 2006/0132790 | A1 | 6/2006 | Gutin | 356/479 |

OTHER PUBLICATIONS

M.A. Choma et al., "Sensitivity advantage of swept source and Fourier domain optical coherence tomography," *Optics Express*, vol. 11, No. 18, Sep. 8, 2003, pp. 2183-2189.

J.F. de Boer et al., "Ultra-High Speed and Ultra-High Resolution Structural, Flow Velocity, and Polarization Sensitive Sd/Fd-Oct and the Human Retina," *ARVO Annual Meeting May 2, 2005, 12:15 P.M-12:30 P.M.*, Program#/Poster#: 1116, printed from website, http://www.abstractsonline.com/viewer/ViewAbstractPrintFriendly on Jul. 26, 2005, 2 pages in length.

R.D. Ferguson et al., "Enhanced Retinal Imaging With Tracking Optical Coherence Tomography (TOCT)," *ARVO Annual Meeting May 2, 2005, 12:45 P.M.-1 P.M.*, Program#/Poster#: 1118, printed from website, http://www.abstractsonline.com/viewer/ViewAbstractPrintFriendly on Jul. 26, 2005, 1 page in length.

J.G. Fujimoto, "New Technology for Optical Coherence Tomography" [table of contents title 'Advances in High Resolution and Spectral OCT'], *Ocular Imaging 2005*, Palm Beach, Florida, Dec. 3-4, 2004, at 11:00 a.m., 8 pages in length.

G. Gregori et al., "3-D OCT Maps in Retinal Pathologies," *ARVO Annual Meeting May 2, 2005,10 A.M.-10:15 A.M.*, Program#/Poster#: 1055, printed from website, http://www.abstractsonline.com/viewer/ViewAbstractPrintFriendly on Jul. 26, 2005, 1 page in length.

C.K. Hitzenberger et al., "Three-dimensional imaging of the human retina by high-speed optical coherence tomography," *Optics Express*, vol. 11, No. 21, Oct. 20, 2003, pp. 2753-2761.

D. Huang et al., "Optical Coherence Tomography," *Science*, vol. 254, Nov. 22, 1991, pp. 1178-1181.

J.A. Izatt et al., "Ophthalmic Diagnostics using Optical Coherence Tomography," Ophthalmic Technologies III, *SPIE*, vol. 1877, Jan. 16-18, 1993 (Los Angeles, CA), pp. 136-144.

S. Jiao et al., Powerpoint presentation "Simultaneous acquisition of sectional and fundus images with spectral-domain optical coherence tomography," Photonics West, Jan. 22, 2005, *Ophthalmic Technologies XV*, Program #5688-81, 21 pages in length.

S. Jiao et al., "Simultaneous acquisition of sectional and fundus ophthalmic images with spectral-domain optical coherence tomography," *Optics Express*, vol. 13, No. 2, Jan. 24, 2005, pp. 444-452.

S. Jiao et al., "Macula Mapping and Simultaneous Acquisition of Sectional and Fundus Ophthalmic Images With Three-Dimensional Spectral-Domain Optical Coherence Tomography," *ARVO Annual Meeting May 2, 2005, 11:45 A.M.- 12 P.M.*, Program#/Poster#: 1114, printed from website, http://www.abstractsonline.com/viewer/ViewAbstractPrintFriendly on Jul. 26, 2005, 1 page in length.

T.H. Ko et al., "Three Dimensional Retinal Imaging of Small Animals With High-speed, Ultrahigh Resolution Optical Coherence Tomography," *ARVO Annual Meeting May 2, 2005, 9A.M.-9:15 A.M.*, Program#/Poster#: 1051, printed from website, http://www.abstractsonline.com/viewer/ViewAbstractPrintFriendly on Jul. 26, 2005, 1 page in length.

C.A. Puliafito, "Summary and Significance," *American Academy of Ophthalmology Subspecialty Day on retina, Section X: Ocular Imaging*, New Oreleans, Oct. 23, 2004, 3:06 P.M., 16 pages in length.

S. Sacu et al., "Imaging and Pigment Epithelial Disease Using Threedimensinoal (3D) Ultrahigh Resolution (UHR) Optical Coherence Tomography (OCT)," *ARVO Annual Meeting May 3, 2005, 11:15 A.M.- 1 P.M.*, Program#/lPoster#: 2563/B116, printed from website, http://www.abstractsonline.com/viewer/ViewAbstractPrintFriendly on Jul. 26, 2005, 1 page in length.

U.M. Schmidt-Erfurth et al., "Three-Dimensional Ultrahigh Resolution Optical Coherence Tomography (3D UHR OCT): A Video Presentation," *ARVO Annual Meeting May 2, 2005, 12 P.M.-12:15 P.M.*, Program#/Poster#: 1115, printed from website, http://www.abstractsonline.com/viewer/ViewAbstractPrintFriendly on Jul. 26, 2005, 1 page in length.

C.D. Scholda et al., "Visualization of the Vitreoretinal Interface Using Three-Dimensional Ultrahigh Resolution Optical Coherence Tomography," *ARVO Annual Meeting May 2, 2005, 9:45 A.M.-10 A.M.*, Program#/Poster#: 1054, printed from website, http://www.abstractsonline.com/viewer/ViewAbstractPrintFriendly on Jul. 26, 2005, 1 page in length.

P.F. Sharp, "The scanning laser ophthalmoscope—a review of its role in bioscience and medicine," *Physics in Medicine and Biology*, vol. 49 (2004), pp. 1085-1096.

V.J. Srinivasan et al., "Intraretinal Thickness Mapping using Three-Dimensional, High-Speed Ultrahigh Resolution OCT," *ARVO Annual Meeting May 2, 2005, 11:30 A.M.-11:45 A.M.*, Program#/Poster#: 1113, printed from website, http://www.abstractsonline.com/viewer/ViewAbstractPrintFriendly on Jul. 26, 2005, 1 page in length.

K.A. Swanson et al., "In vivo retinal imaging by optical coherence tomography," *Optics Letters*, vol. 18, No. 21, Nov. 1, 1993, pp. 1864-1866.

J.S. Werner et al., "Three-Dimensional Retinal Imaging With High Speed and High Resolution OCT," *ARVO Annual Meeting May 2, 2005, 9:15 A.M.-9:30 A.M.*, Program#/Poster#: 1052, printed from website, http://www.abstractsonline.com/viewer/ViewAbstractPrintFriendly on Jul. 26, 2005, 1 page in length.

M. Wojtkowski et al., "Three-dimensional Retinal Imaging with High-Speed Ultrahigh-Resolution Optical Coherence Tomography," *American Academy of Ophthalmology* (2005), pp. 1-14.

M. Wojtkowski et al., "Ophthalmic Imaging by Spectral Optical Coherence Tomography," *American Journal of Ophthalmology*, Ophthalmic Publ., Chicago, IL, vol. 138, No. 3, Sep. 2004, pp. 412-419.

M.A. Choma, "Sensitivity advantage of swept source and Fourier domain optical coherence tomography," *Optics Express*, vol. 11, No. 18, Sep. 8, 2003, pp. 2183-2189.

M. Wojtkowski et al., "Three-dimensional Retinal Imaging with High-Speed Ultrahigh-Resolution Optical Coherence Tomography," *American Journal of Ophthalmology*, Ophthalmic Publ., Chicago, Illinois (Sep. 2004), 13 pages in length.

* cited by examiner

ENHANCED OPTICAL COHERENCE TOMOGRAPHY FOR ANATOMICAL MAPPING

PRIORITY

This application is a continuation of U.S. patent application Ser. No. 11/975,239, filed Oct. 18, 2007, which in turn is a continuation of U.S. patent application Ser. No. 11/219,992, filed Sep. 6, 2005, which in turn claims priority from U.S. Provisional Application Ser. No. 60/632,387, filed Dec. 2, 2004, the disclosure of which is incorporated herein by reference.

BACKGROUND OF THE INVENTION

1. Technical Field

The present invention relates to coherent waveform based imaging, and more particularly to an optical coherence tomography (OCT) imaging system.

2. Statement of the Related Art

Many imaging systems utilize coherent waveforms to obtain information regarding target objects of interest. Examples include OCT, ultrasound diagnostics, and synthetic aperture radar. OCT is a low-coherence interferometer-based noninvasive medical imaging modality that can provide high-resolution sectional images of biological tissues (see for example, U.S. Pat. No. 5,321,501, U.S. Pat. No. 5,459,570, Huang, D. et al. (1991). "Optical coherence tomography." *Science* 254(5035): 1178-81). Since first introduced, OCT has been used in a variety of medical research and diagnostic applications. One successful application of OCT imagery can include the use of OCT in the dermatological imaging of the skin. Another successful application of OCT imagery can include sectional imaging of the retina in the field of ophthalmology. In this regard, time domain based OCT has produced cross-sectional images of the retina of the eye that have proven value to ophthalmologists (see for example, Swanson, E. A. et al. (1993). "In-vivo retinal imaging by optical coherence tomography." *Optics Letters* 18(21): 1864-1866; Izatt, J. A. et al. (1993). "Ophthalmic diagnostics using optical coherence tomography". Ophthalmic Technologies III, SPIE, 1877: 136-144, Los Angeles, Calif., USA). Notwithstanding, time domain OCT instruments cannot acquire sufficient data to characterize completely important retinal pathologies.

The limitations of time domain OCT are the natural result of the inherent difficulties in acquiring and processing imagery of an unstable target—the human eye. For example, although ophthalmic OCT has been commercialized for several years, the spatial registration of an OCT image to fundus landmarks has not been achieved satisfactorily. In this regard, fundus landmarks can be used to relate different structural abnormalities at different retinal locations. Precise spatial registration of OCT sections to tissue location also can be important when interpreting other medical images. Yet, the unavoidable eye movement of a patient during image acquisition can complicate the ability to achieve precise spatial registration due to the unavoidable distortion of the OCT image.

As an alternative to OCT, the scanning laser ophthalmoscope (SLO) provides en face fundus images familiar to ophthalmologists (see for example, Sharp, P. F. et al (2004) "The scanning laser opthalmoscope—a review of its role in bioscience and medicine" *Physics in Medicine and Biology* 49: 1085-1096). In this regard, en face views are familiar to ophthalmologists not only from direct observations, but also from fundus photographs and fluorescein angiography. The strength of an en face view is that structural abnormalities at different retinal locations can be related to each other and to major retinal landmarks such as the fovea and optic nerve head. In any case, combining OCT with SLO (SLO/OCT) provides one possible means for precise spatial registration of the OCT image while providing an en face fundus image (see for example, U.S. Pat. No. 5,975,697, U.S. Pat. No. 6,769,769, CA2390072, US20040036838, US20040233457, and WO2004102112).

Specifically, time domain SLO/OCT systems utilize two-dimensional transverse scans to provide sectional images in planes perpendicular to the depth of the sample. In an SLO/OCT system, the fundus image can be acquired by splitting the reflected sample light during the transverse scan into two detection channels. A first channel can accommodate OCT while the second channel can be utilized in acquiring intensity image (see for example, U.S. Pat. No. 5,975,697, U.S. Pat. No. 6,769,769, CA2390072, US20040036838, US20040233457, and WO2004102112). As an alternative approach, the sectional images can be summed along the depth of the image (see for example, Hitzenberger, C. K. et al. (2003). "Three-dimensional imaging of the human retina by high-speed optical coherence tomography." *Optics Express* 11(21): 2753-2761; Puliafito C. A. "Summary and Significance" American Academy of Opthalmology Subspecialty Day on retina, Section X: Ocular Imaging, New Orleans, Oct. 23, 2004, 3:06 pm). The approach of two detection channels can require a more complicated setup and the signal-to-noise ratio of the OCT may be reduced by a partial sacrifice of the back-reflected sample light. By comparison, in the approach of summing the OCT images along their depth, accuracy can be sacrificed when the eye moves between different sections.

SUMMARY OF THE INVENTION

The present invention is an OCT method, system and apparatus which addresses the foregoing deficiencies of time domain ocular imaging. In particular, what is provided is a novel method, system and apparatus for anatomical mapping using spectral domain OCT. As well, time-domain OCT and swept source frequency OCT also can be applied to provide the enhanced anatomical mapping of the present invention. In this invention, the term spectral domain OCT (SD-OCT) is sometimes used to include both spectrometer based spectral or Fourier domain OCT, and tunable laser based swept source OCT since their basic principle of operation is very similar (see for example, Choma, M. A. et al. (2003). "Sensitivity advantage of swept source and Fourier domain optical coherence tomography." *Optics Express* 11(18): 2183-2189). In accordance with the present invention, a fundus intensity image can be acquired from a spectral domain scanning of light back-reflected from an eye. The term "intensity image" as defined in this invention is a two-dimensional en-face image extracted from a 3D OCT data block by integrating the OCT signal over a depth range (Z-axis) greater than the axial resolution of the OCT system. For example, a fundus image can be extracted by the method disclosed herein from OCT data covering the fundus of the human eye. The fundus intensity image actually represents a reduction in total information content. Specifically, the squaring and summing over the spectra results in a loss of all depth information. Yet, the loss of depth information can achieve a shortcut to a particularly useful item of distilled information for the purpose of medical diagnostics.

A 3-D OCT data set can be reduced to generate an ocular mapping, including edema mappings and thickness mappings. Optionally, a partial fundus intensity image can be produced from the spectral domain scanning of the eye to generate an en face view of the retinal structure of the eye without first requiring a full segmentation of the 3-D OCT data. The partial intensity image is a two-dimensional en-face image extracted from a 3D OCT data block by integrating the OCT signal over a depth range greater than the axial resolution of the OCT system, but including only selected regions of the 3-D anatomical structure for integration.

The present invention can differ from conventional, time domain OCT technology because the mapping system of the present invention can be optimized to obtain the information necessary for assessing macular edema while simultaneously producing a fundus intensity image. As part of the optimization, the present invention utilizes optimized sampling grids. For example, in the case of volume measurements of fluid-filled spaces, which require several samples spread over the areal extent of the space, a raster scan can be utilized having evenly spaced points on a square grid.

Importantly, in accordance with the present invention, the data set acquired by the spectral domain scan can contain all of the 3-D information about retinal structure needed to estimate the volumes of fluid-filled spaces. Accordingly, 3-D segmentation algorithms can be applied to the intensity data set to outline spatial structures. As yet another important aspect of the invention, intensity information can be extracted from each measured spectrum to provide an en face view or an image of the fundus that can be used immediately to judge image data quality. In this regard, an operator can then decide whether or not to take another image. Because the intensity image is generated from the same data as the subsequent 3-D data set, the intensity image provides all necessary landmarks for precisely locating on the fundus the lesions revealed by the cross-sectional OCT scan. The intensity image also provides the landmarks needed for orienting the 3-D data set to other fundus images, such as fundus photographs and fluorescein angiograms.

As an additional advantage, because the fundus intensity image can be generated before segmentation of the 3-D data set, the fundus intensity image can be used to guide the segmentation. For example, retinal blood vessels represent discontinuities in the layered retinal architecture that often disrupt segmentation of cross-sectional images. The fundus intensity image can be processed by ordinary 2-D algorithms to identify the blood vessel positions. Subsequent processing of the OCT cross-sectional images then can be modified at each vessel location. For instance, an algorithm designed to follow layers can skip past a vessel and resume segmentation on the other side of the vessel. Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

The present invention is a system, method and apparatus for anatomical mapping through the production of a 3-D data set, for instance through imagery produced utilizing OCT. In accordance with the present invention, a fundus intensity image can be acquired from a spectral domain scanning of light back-reflected from an eye. The 3-D data set can be reduced to generate an ocular mapping, including edema mappings and thickness mappings. Optionally, a partial fundus intensity image can be produced from the spectral domain scanning of the eye to generate an en face view of the retinal structure of the eye without first requiring a full segmentation of the 3-D data set.

Figure 1:
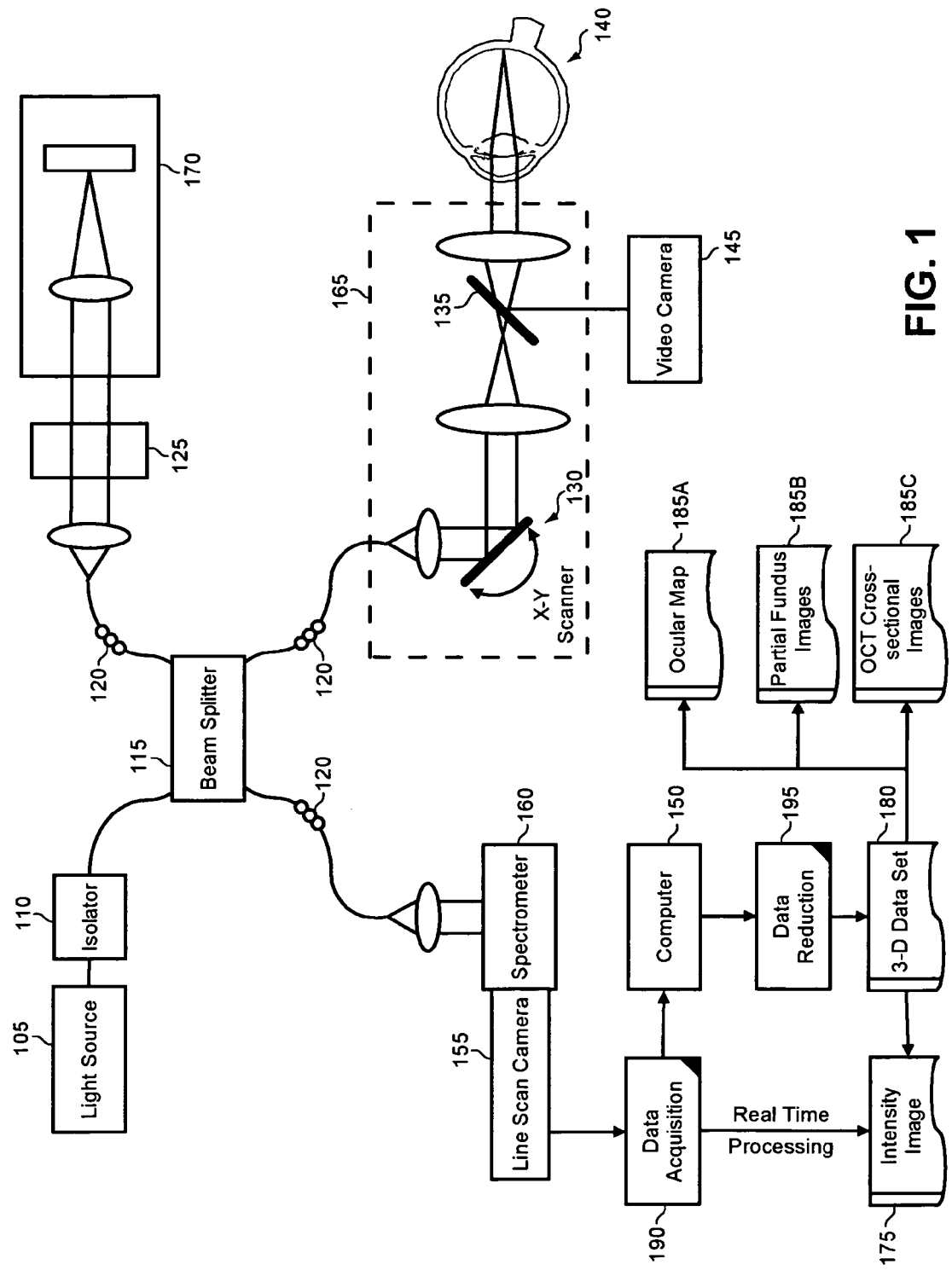
FIG. 1 is a schematic illustration of an OCT imaging system configured for anatomical mapping in accordance with the present invention; and, FIG. 2 is a flow chart illustrating a process for anatomical mapping in the OCT imaging system of FIG. 1.

In further illustration, FIG. 1 is a schematic illustration of an OCT imaging system configured for anatomical mapping in accordance with the present invention. As shown in FIG. 1, a low coherent light source 105 can be provided. The low coherent light source 105 can be a super-luminescent diode, such as a super-luminescent diode having a center wavelength sufficient to penetrate the vitreous portions of the eye 140—typically between 800 and 900 nm. In this context, those skilled in the art consider such a light source as a broadband light source. The light source 105 can be coupled to a beam splitter 115 by way of optional fiber-based isolator 110.

Specifically, the beam splitter 115 can be a 2×2 3 dB fiber coupler configured to split light emanating from the light source 105 into sample and reference arms. The sample arm can be coupled into the optical head of a light delivery system 165. The light delivery system 165 can include an x-y scanner 130 and optics for delivering the sample light into the eye 140 and collecting the back-reflected sample light. Optionally, the back-reflected sample light can be partially reflected through operation of a dichroic mirror 135 into a video camera 145 for real time viewing of the fundus.

By comparison to the sample arm, the reference arm can include a variable neutral density filter 125 used to adjust the reference intensity before and after the light reaches the optical reference system 170. Polarization controllers 120 can be used in both the reference and sample arms for fine tuning of the sample and reference polarization states to achieve maximal interference. In an exemplary configuration of the detection arm, a spectrometer 160 can be coupled to a line scan camera 155 to detect the combined reference and sample light. As is known in the art, a spectrometer will include an optical element such as a diffraction grating for angularly dispersing the light as a function of wavelength. The dispersed light falls on the pixels of the line scan camera. The light intensities measured by the camera pixels contain information corresponding to the distribution of reflection sites along the Z-axis depth in the sample.

Both the line scan camera 155 and the video camera 145 can be communicatively linked to a computer 150. The computer 150 can be coupled both to a data acquisition processor 190 configured to acquire data from the line scan camera 155, and also to a data reduction processor 195 configured to reduce the acquired data to produce anatomical maps 185A and partial fundus imagery 185B. The 3-D data sets would also be used to create cross-sectional OCT images 185C as known in the art.

By operation of the data acquisition processor 190, both a 3-D data set 180 and an intensity image 175 can be acquired. The intensity image 175 can be acquired in real time directly from the data acquisition processor using either digital or analog processing. Complex data processing associated with generating OCT images is not required. Consequently, an operator can discard the image if it is determined that the image is of too low quality without permitting further data processing. The 3-D data set 180, by comparison, can be produced by operation of the data reduction processor 195 from the image acquired by the data acquisition process 190. Notably, an intensity image 175 can also be derived from the 3-D data set. An intensity image created either directly from the data acquisition or from the 3-D data set can be useful for data registration to other imaging modalities. Moreover, blood vessels can be identified as an initial step in a segmentation process. In a swept source spectral domain OCT embodiment, the output wavelength of the light source can be varied or scanned, for example, via frequency modulation. Only a single photodetector is required rather than a spectrometer and a line scan camera. The intensity data as a function of wavelength is extracted over time.

Figure 2:
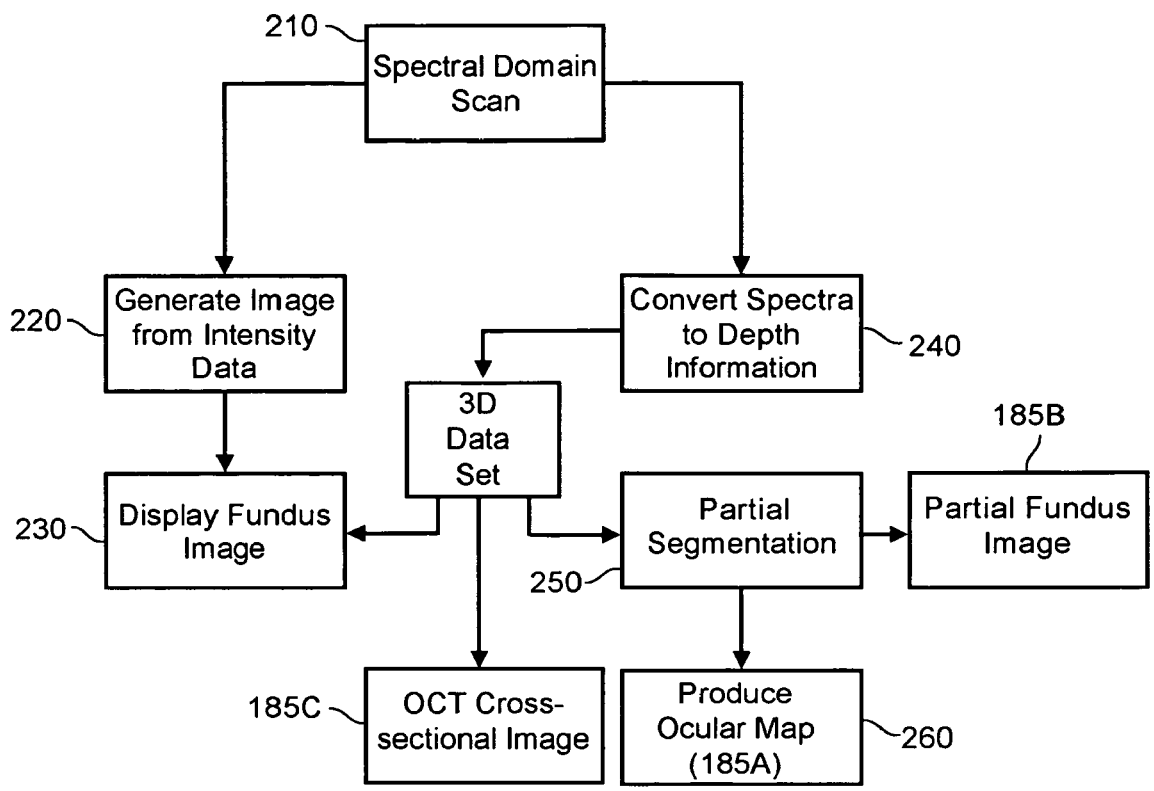

In a more particular illustration, FIG. 2 is a flow chart illustrating a process for anatomical mapping in the OCT imaging system of FIG. 1. Beginning first in block 210, the inherent speed of a spectral domain OCT can be utilized to sample the entire macula of an eye on a square grid. In a specific aspect of the invention, a total of 65,536 a-scans can be collected in slightly over one second by following a left-to-right, top-to-bottom scan pattern in which adjacent a-scans are separated by 23 µm, which provides adequate lateral resolution to sample fluid-filled spaces of the eye.

In block 220, a fundus image can be generated directly from intensity data included within the spectra produced by the spectral domain scan. In this regard, it is to be noted that each captured spectrum contains at least two components from which can be extracted a signal proportional to the total reflected intensity. This intensity signal can be used to produce a 2-D image of the fundus that advantageously can appear similar to the image from an SLO. Various methods can be employed to obtain the intensity signal in "real-time", so that the fundus image can be painted on a display screen as rapidly as it is acquired.

The method for extracting intensity information can be understood by considering the primary mathematical expression for the spectral intensity of the interference fringes falling on the line scan camera:

$$G_d(v) = G_s(v) \left\{ 1 + \sum_n R_{sn} + 2 \sum_{n \neq m} \sqrt{R_{sn} R_{sm}} \cos[2\pi v(\tau_n - \tau_m)] + 2 \sum_n \sqrt{R_{sn}} \cos[2\pi v(\tau_n - \tau_r)] \right\},$$

where v is the frequency of the light; $R_{sn}$ is the intensity reflection of a small region in the sample; $G_s(v)$ is the spectral density of the light source; the reflection of the reference arm is unity; distances are represented by propagation times $\tau_n$, $\tau_m$ in the sample arm and $\tau_r$ in the reference arm and summation is across all axial depths in the sample beam. The third term in brackets is the mutual interference for all light scattered within the sample and the last term contains the interference between the scattered sample light and the reference light from which an a-scan is calculated. It is important to note that, in embodiments where the detector is a spectrometer, the parameter v also represents position on the line scan camera. Hence, the primary equation can be broken conceptually into two parts: the first two terms represent slow variation across the linear array of camera pixels while the last two terms represent oscillations (interference fringes). Similarly, in the embodiments where the source is swept through a range of frequencies v the first two terms in the primary equation represent slow variation in time of the detected signal, while the last two terms represent oscillations.

The new insight that leads to generation of a fundus image is to recognize that the desired information about total reflected sample intensity resides in both the second and fourth terms of the primary equation. This permits multiple methods for extracting the intensity. The method selected for a particular application will depend on desired speed and accuracy. Several examples of methodologies for obtaining a fundus intensity image follow in which F(x,y) is the output of the processing method for an a-line at scan point x,y on the fundus.

In a first example, the primary equation can be summed across v (in practice, across the pixels of the line scan camera). Notably, the cosine terms in the primary equation which have many cycles across the spectrum will sum to (approximately) zero. Thus, applying the summation can yield $$F(x, y) = \overline{G}_s \left( 1 + \sum_n R_{sn} \right),$$

where $\overline{G}_s$ is the total source power. The first term can, in principle, be ignored for display purposes leaving $$\sum_n R_{sn},$$

which is proportional to the sum of all reflected intensities in the sample, i.e., the desired fundus intensity. Digital summation of the camera output can be very fast and this method may be most suitable for painting the fundus image into a display window as rapidly as it is acquired. Various techniques can be used, if necessary, to compensate for small variations in $\overline{G}_s$ with x,y. It is clear that other low-pass filter techniques besides simple summation can also be applied to the primary equation to yield the above result.

In another example, the fundus intensity can also be derived from the fourth term of the primary equation by separating the oscillatory component from the slow variation and recognizing that, for retina and other low reflectance samples, the third term is small relative to the fourth term. One method to achieve this is to apply a Fourier transform to the primary equation, to discard the low frequency terms, and then to square and sum the high frequency terms. By Parseval's theorem this is equivalent in the camera output signal to high pass filtering the primary equation to remove the low frequency component, then squaring the remaining oscillatory component and summing over the spectrum.

Neglecting the third term of the equation, the high pass filtering, squaring and summing of the primary equation can produce:

$$F(x, y) = \sum_{v}\left\{2\sum_{n}\sqrt{R_{sn}}\,G_s(v)\cos[2\pi v(\tau_n - \tau_r)]\right\}^2 = 4\overline{G_s^2}\sum_{n} R_{sn},$$

which can be displayed directly to produce an intensity image. It is noted that one can modify the parameters of the high-pass filter in order to change the contrast of the fundus image by changing the relative contributions of shallower and deeper structures. The choice of domain in which to operate depends on considerations of speed and ease of implementation. Operations on the camera output can be carried out digitally or, for highest speed, by analog processing. Similarly, in a third exemplary method for obtaining a fundus intensity image, the observation that a spectrometer normally discards the zero order beam can be utilized such that the intensity of the zero order beam also can have the form of the equation yielded by the summation of the primary equation. Thus, the intensity signal can be obtained directly with an auxiliary photodetector and displayed with conventional methods.

Returning now to FIG. 2, regardless of how the fundus intensity image is generated, in block 230 the fundus intensity image can be displayed. In this regard, the fundus intensity image can provide a plurality of benefits. First, the display of the fundus intensity image can provide immediate feedback on scan quality to the operator. Scans contaminated by eye movements, blinks or other artifacts can be repeated before data processing. Second, because the fundus intensity image is generated from the same data as the subsequent 3-D data set, the fundus intensity image can provide all necessary landmarks for orienting the 3-D data to other fundus images, such as fundus photographs and fluorescein angiography. Third, the fundus intensity image serves to locate features that are seen in cross-sectional images.

In block 240, the acquired set of spectral domain scans can be converted into a data set that contains the axial (Z-axis) reflectance of the sample. As part of the conversion process, the acquired spectra can be transformed from points linear in wavelength to points linear in frequency (wave number). This transformation can be accomplished mathematically. Alternatively, the transformation can be accomplished by building a line scan camera that has unequally-spaced pixels. Specifically, the modified line scan camera can incorporate pixels spaced according to the reciprocal of the distance along the light detector chip in the camera. The consequent variation in pixel size will cause variation in pixel gain, but this can be compensated electronically or digitally. The transformation would therefore take place instantly in hardware, greatly speeding up the generation of the spatial data. The product of the transformation may then be used in the conversion 240 to produce a set of Z-axis intensity information data for each unique X and Y position of the beam on the sample, i.e. a 3-D data set. As noted above, this 3-D data can be converted directly into a full intensity image, for example, by squaring and summing the intensity data at each X/Y position. The 3-D data is also used to generate conventional OCT cross-sectional images 185C. The 3-D data can also be subjected to a partial segmentation process (block 250) in order to outline and quantify fluid-filled spaces and other retinal features. This segmented data can also be used (block 260), to generate ocular maps, such as "edema maps" and "thickness maps" that can be used for diagnosis and treatment. The partial segmentation can also be used to generate a partial fundus image. The partial fundus image is generated the same way as the full fundus image from the 3-D data however, the depth location and range around that depth is limited and selected through the segmentation process. As discussed below, a partial fundus image can be created to highlight certain features or landmarks in the eye. Note that a full segmentation process would be one that identifies many (or all) retinal layers and/or structures. A partial fundus image requires finding only one surface, either a specific retinal layer, like the retinal pigment epithelium, or a more general description of retinal tilt and curvature such as the locus of the centroids of each a-scan.

Notably, the retina can be tilted and curved with respect to the Cartesian coordinate system of the acquired 3-D data set. Reference surfaces identified during segmentation can be used as boundaries to create a partial intensity image that help identify the tilt and curvature. The reference surfaces can capture this tilt and curvature as mathematical surfaces within the acquired data set. These reference surfaces can be generated by combining lines segmented on individual longitudinal cross sectional scans (B-scans). Reference surfaces also can typically correspond to known anatomical layers of the retina. Likely examples include the retinal pigment epithelium (RPE) and the inner limiting membrane (ILM). The reference surfaces can be used to visualize pathology or to define layers within the data set that have the variation due to retinal tilt and curvature removed. Data points within these layers can be used to form en face images or partial intensity images that represent retinal structures localized to a particular depth or anatomic layer.

A characteristic of the data set for the partial fundus intensity image is that it has thickness, in general greater than the axial resolution of the OCT. This and the fact that the layer is curved and tilted in a way intended to capture anatomy distinguishes it from "C-scans"—the tangential slices produced by SLO/OCT instruments—which are perpendicular to the scanning beam. Hence, C-scans are thin, the thickness being defined by the axial resolution, and they are not usually aligned with retinal structures.

Specifically, intensity in axial scans can be expressed as $$I(\tau) = 2\sum_{n}\sqrt{R_n}\,\Gamma\left[\tau \pm 2(\tau_n - \tau_r)\right],$$

where distance along the z-axis is represented by propagation time $\tau = nz/c$ with n the refractive index of tissue and c the speed of light in vacuum; $\tau_n$ and $\tau_r$ are the propagation times for light reflected by the nth scatterer in the sample and the reference mirror, respectively; $R_n$ is the normalized intensity reflection of the nth scatterer; and summation is across all axial depths in the sample beam. $\Gamma(\tau)$ is the autocorrelation function of the light source and expresses the axial resolution of the system. Note $\Gamma[\tau \pm 2(\tau_n - \tau_r)]$ falls rapidly to zero as $(\tau_n - \tau_r)$ becomes greater than the axial resolution. For each depth $\tau$, therefore, the reflected intensity comes from only a thin layer of the $R_n$.

Thus, a tissue layer defined as above can be expressed by its upper boundary $\tau_0(x, y)$ and lower boundary $\tau_1(x, y)$. The total reflectance of the scatterers in the tissue layer at each point (x,y) can be obtained by squaring $$I(\tau) = 2\sum_{n}\sqrt{R_n}\,\Gamma\left[\tau \pm 2(\tau_n - \tau_r)\right],$$

and then summing from $\tau_0$ to $\tau_1$. The result is the desired partial fundus intensity image $$F(x, y) = \sum_{r_0}^{r_1} \left\{ 2 \sum_n \sqrt{R_n} \, \Gamma \left[ \tau \pm 2(\tau_n - \tau_r) \right] \right\}^2.$$

Still, it is to be understood that the partial fundus intensity image (as well as the fundus intensity image) can be obtained without the explicit use of the above equation. In fact, any monotonic transformation of the a-line intensities, when summed, can produce an apparent partial fundus intensity image, though the relative intensities of the different structures can differ. For example, the squaring step can be omitted prior to the summing step and the resulting partial fundus intensity image can suffice. In fact, performing a monotonic transformation, strictly speaking, is not required as a transformation having a "little wiggle" can provide a similar result. Notwithstanding, the above equation can provide a true intensity and serves as a preferred example of the technique. Note that the generation of a partial fundus image need not be restricted to a summation between two surfaces, but could also be defined by an integral under a z-profile that followed the reference surface, (e.g., the two surface example defines a rectangular z-profile).

The partial fundus intensity image can be applied to the registration of OCT with other modalities. Specifically, in addition to its use for display of pathology, a partial fundus intensity image can be used to provide high contrast images of the retinal blood vessels that are useful for aligning the OCT data set to images from other clinical modalities (such as fundus photographs). Due to scattering by red blood cells, major retinal blood vessels cast strong shadows onto the underlying tissue. By placing one boundary of the slab a distance below the ILM that excludes the light scattered by the blood vessels themselves, then forming the partial fundus intensity image from all tissue below that boundary, these shadows are emphasized and the blood vessel pattern stands out in stark relief against the brighter retinal reflection. This type of partial fundus intensity image can be referred to as a shadowgram as other partial fundus intensity images can be used to emphasize intra-retinal or sub-retinal structures by the reflected light of the structures rather than the shadows produced by the incidence of light upon the structures.

The fundus intensity image also solves the specific problem of image registration for assessment of the retinal nerve fiber layer in glaucoma diagnosis. In the case of the retinal nerve fiber layer, more accurate registration will reduce measurement variance and improve the detection of glaucoma progression.

The method of the present invention can be realized in hardware, software, or a combination of hardware and software. An implementation of the method of the present invention can be realized in a centralized fashion in one computer system, or in a distributed fashion where different elements are spread across several interconnected computer systems. Any kind of computer system, or other apparatus adapted for carrying out the methods described herein, is suited to perform the functions described herein.

A typical combination of hardware and software could be a general purpose computer system with a computer program that, when being loaded and executed, controls the computer system such that it carries out the methods described herein. The present invention can also be embedded in a computer program product, which comprises all the features enabling the implementation of the methods described herein, and which, when loaded in a computer system, is able to carry out these methods.

Computer program or application in the present context means any expression, in any language, code or notation, of a set of instructions intended to cause a system having an information processing capability to perform a particular function either directly or after either or both of the following a) conversion to another language, code or notation; b) reproduction in a different material form. Significantly, this invention can be embodied in other specific forms without departing from the spirit or essential attributes thereof, and accordingly, reference should be had to the following claims, rather than to the foregoing specification, as indicating the scope of the invention.

The following references are incorporated herein by reference:

US Patent Documents

U.S. Pat. No. 5,321,501
U.S. Pat. No. 5,459,570
U.S. Pat. No. 5,975,697
U.S. Pat. No. 6,769,769
US20040036838
US20040233457

Foreign Patent Documents

CA2390072
WO2004102112

Other Publications

Bower, B. A. et al. "Rapid Volumetric Imaging of the Human Retina in vivo Using a Low-Cost, Spectral-Domain Optical Coherence Tomography System" ARVO annual meeting, May 2, 2005, 8:45 AM-9:00 AM, #1050

Choma, M. A. et al. (2003). "Sensitivity advantage of swept source and Fourier domain optical coherence tomography." Optics Express 11(18): 2183-2189 de Boer, J. F. et al. "Ultra-High Speed and Ultra-High Resolution Structural, Flow Velocity, and Polarization Sensitive Sd/Fd-Oct of the Human Retina" ARVO annual meeting, May 2, 2005, 12:15 PM-12:30 PM, #1116

Ferguson, R. D. et al. "Enhanced Retinal Imaging With Tracking Optical Coherence Tomography (TOCT)" ARVO annual meeting, May 2, 2005, 12:45 PM-1:00 PM, #1118

Fujimoto, J. "Advances in High Resolution and Spectral OCT" Ocular Imaging 2005, Palm Beach, Fla., Dec. 4, 2005, 11:00 am Gregori, G. et al. "3-D OCT Maps of Retinal Pathologies" ARVO annual meeting, May 2, 2005, 10:00 AM-10:15 AM, #1055

Hitzenberger, C. K. et al. (2003). "Three-dimensional imaging of the human retina by high-speed optical coherence tomography." Optics Express 11(21): 2753-2761

Huang, D. et al. (1991). "Optical coherence tomography." Science 254(5035): 1178-81

Izatt, J. A. et al. (1993). "Ophthalmic diagnostics using optical coherence tomography". Ophthalmic Technologies III, SPIE, 1877: 136-144, Los Angeles, Calif., USA Jiao, S., et al. "Simultaneous acquisition of sectional and fundus ophthalmic images with spectral-domain optical coherence tomography" Photonics West, Jan. 22, 2005, Ophthalmic Technologies XV, Program #5688-81.

Jiao, S. et al. (2005) "Simultaneous acquisition of sectional and fundus ophthalmic images with spectral-domain optical coherence tomography" *Optics Express* 13, 444-452, Jiao, S. et al. "Macula Mapping and Simultaneous Acquisition of Sectional and Fundus Ophthalmic Images With Three-Dimensional Spectral-Domain Optical Coherence Tomography" ARVO annual meeting, May 2, 2005, 11:45 AM-12:00 PM, #1114

Ko, T. H. et al. "Three Dimensional Retinal Imaging of Small Animals With High-speed, Ultrahigh Resolution Optical Coherence Tomography" ARVO annual meeting, May 2, 2005, 9:00 AM-9:15 AM, #1051

Puliafito C. A. "Summary and Significance" American Academy of Opthalmology Subspecialty Day on retina, Section X: Ocular Imaging, New Orleans, Oct. 23, 2004, 3:06 pm Sacu, S. et al. "Imaging of Pigment Epithelial Disease Using Three-dimensional (3D) Ultrahigh Resolution (UHR) Optical Coherence Tomography (OCT)" ARVO annual meeting, May 3, 2005, 11:15 AM-1:00 PM, #2563/B116

Schmidt-Erfurth, UM et al. "Three-Dimensional Ultrahigh Resolution Optical Coherence Tomography (3D UHR OCT): A Video Presentation" ARVO annual meeting, May 2, 2005, 12:00 PM-12:15 PM, #1115

Scholda, C. D. et al. "Visualization of the Vitreoretinal Interface Using Three-Dimensional Ultrahigh Resolution Optical Coherence Tomography" ARVO annual meeting, May 2, 2005, 9:45 AM-10:00 AM, #1054

Sharp, P. F. et al (2004) "The scanning laser opthalmoscope—a review of its role in bioscience and medicine" *Physics in Medicine and Biology* 49: 1085-1096)

Srinivasan, V. J. et al. "Intraretinal Thickness Mapping using Three-Dimensional, High-Speed Ultrahigh Resolution OCT" ARVO annual meeting, May 2, 2005, 11:30 AM-11:45 AM, #1113

Swanson, E. A. et al. (1993). "In-vivo retinal imaging by optical coherence tomography." *Optics Letters* 18(21): 1864-1866;

Werner, J. S. et al. "Three-Dimensional Retinal Imaging With High Speed and High Resolution OCT" ARVO annual meeting, May 2, 2005, 9:15 AM-9:30 AM, #1052

What is claimed is:

1. A method for generating a partial fundus image from a 3-D data set defined by Z-axis intensity information for a plurality of X and Y positions acquired by scanning the eye with an optical coherence tomographic (OCT) device, said method comprising the steps of:
    applying to a portion of said intensity information acquired by scanning the eye with an optical coherence tomographic (OCT) device a substantially monotonic transformation along the Z-axis at each of a plurality of X and Y positions;
    summing the results of the transformation at each of the plurality of X and Y positions over a depth range greater than the axial resolution of the OCT device to create a single transformed intensity value, said portion being selected to isolate a particular anatomical region within the eye; and
    displaying a 2-D image of the transformed intensity values.

2. A method as recited in claim 1, wherein the transformation step is performed by squaring the intensity values.

3. A method as recited in claim 1, wherein the applying and summing steps operate to integrate under a z-profile the intensity values that follow a reference surface.

4. A method as recited in claim 1, wherein the portion of the intensity information is selected by segmenting the information with respect to a reference surface.

5. A method as recited in claim 4 wherein the reference surface is a retinal layer.

6. A method for generating a partial fundus image from a 3-D data set defined by Z-axis intensity information for a plurality of X and Y positions acquired by scanning the eye with an optical coherence tomographic (OCT) device, said method comprising the steps of:
    identifying a reference surface within the eye from the 3-D data set which was acquired by scanning the eye with an optical coherence tomographic (OCT) device;
    integrating under a z-profile the intensity information that follows the reference surface to create a single intensity value at a plurality of X and Y positions; and
    displaying a 2-D image of the integrated intensity values.

7. An apparatus for obtaining images of an object comprising:
    a spectral domain optical coherence tomography (OCT) system, said system including a light source, a beam splitter for dividing the light along a sample path and a reference path, said sample path further including a scanner for scanning the light in at least one of the X and Y directions over the sample;
    a detector having a linear array of detector elements for receiving light returned from both the sample and the reference paths and generating a plurality of sets of outputs, each set corresponding to varying intensities at different frequencies of said source at a particular X/Y position of said light on said sample, said intensities including information about the reflection distribution along the sample in the Z axis, wherein said detector elements are positioned so that output therefrom is linear in frequency;
    a processor for processing the selected sets of outputs to obtain one or more images of the object.

8. An apparatus as recited in claim 7, wherein the detector elements are unequally positioned along the linear axis of the detector.

9. An apparatus as recited in claim 7, wherein the size of the detector elements is not equal.

10. An apparatus as recited in claim 9 wherein variations in gain related to the different size of the detector elements is compensated.

11. An apparatus as recited in claim 7, wherein the image of the object is an en-face image.

12. An apparatus as recited in claim 11, wherein the en-face image is a partial integration over depth.

13. An apparatus as recited in claim 7, wherein the processor integrates a selected portion of the intensity information over a depth range greater than the axial resolution of the OCT device to create a single intensity value at a plurality of X and Y positions, said portion being selected to isolate a particular anatomical region within the eye, and wherein the image is a 2-D image of the integrated intensity values.

14. A method for generating a partial fundus image from a 3-D data set defined by Z-axis intensity information for a plurality of X and Y positions acquired by scanning the eye with an optical coherence tomographic (OCT) device, said method comprising the steps of:
    integrating a selected portion of the intensity information acquired by scanning the eye with an optical coherence tomographic (OCT) device, said integrating step being carried out over a depth range greater than the axial resolution of the OCT device at a plurality of X and Y positions, said portion being selected to isolate a particular anatomical region within the eye;
    displaying a 2-D image of the integrated intensity values.

15. A method as recited in claim 14, wherein the integrating step generates a single intensity value at each of said plurality of X and Y positions.

16. A method as recited in claim 14, wherein prior to said integrating step, the data is segmented to define a volume as a function of a selected depth within the eye and a selected range from that depth and wherein said integrating step integrates the intensity information along a line extending between the selected depth and the selected range.

17. A method as recited in claim 16, wherein the selected depth corresponds to a landmark within the eye.

18. A method as recited in claim 17, wherein the landmark is a retinal layer.

19. A method as recited in claim 14, wherein prior to said integrating step, a reference surface is identified from within the eye from the 3-D data set wherein said integrating step integrates the intensity information along a line extending between the reference surface and a selected range from that reference surface.

20. A method as recited in claim 19, wherein the reference surface corresponds to an anatomical layer.

* * * * *